US011173617B2

(12) United States Patent
Farritor et al.

(10) Patent No.: US 11,173,617 B2
(45) Date of Patent: Nov. 16, 2021

(54) QUICK-RELEASE END EFFECTOR TOOL INTERFACE

(71) Applicant: Board of Regents of the University of Nebraska, Lincoln, NE (US)

(72) Inventors: Shane Farritor, Lincoln, NE (US); Thomas Frederick, Lincoln, NE (US)

(73) Assignee: BOARD OF REGENTS OF THE UNIVERSITY OF NEBRASKA, Lincoln, NE (US)

(*) Notice: Subject to any disclaimer, the term of this patent is extended or adjusted under 35 U.S.C. 154(b) by 1088 days.

(21) Appl. No.: 15/687,113

(22) Filed: Aug. 25, 2017

(65) Prior Publication Data
US 2018/0056527 A1 Mar. 1, 2018

Related U.S. Application Data

(60) Provisional application No. 62/379,344, filed on Aug. 25, 2016.

(51) Int. Cl.
| A61B 34/30 | (2016.01) |
| B25J 19/00 | (2006.01) |
| B25J 15/04 | (2006.01) |
| A61B 34/00 | (2016.01) |
| A61B 17/00 | (2006.01) |
| H01R 13/00 | (2006.01) |
| H01R 13/625 | (2006.01) |

(Continued)

(52) U.S. Cl.
CPC ..... *B25J 19/0029* (2013.01); *A61B 17/00234* (2013.01); *A61B 34/30* (2016.02); *A61B 34/70* (2016.02); *B25J 15/0408* (2013.01); *H01R 13/005* (2013.01); *H01R 13/625* (2013.01); *H01R 24/20* (2013.01); *A61B 2017/00477* (2013.01); *A61B 2017/2931* (2013.01); *H01R 13/24* (2013.01); *H01R 24/86* (2013.01); *H01R 2107/00* (2013.01); *H01R 2201/12* (2013.01)

(58) Field of Classification Search
CPC ..... A61B 34/30; H01R 13/005; H01R 13/625
See application file for complete search history.

(56) References Cited

U.S. PATENT DOCUMENTS 3,870,264 A 3/1975 Robinson
3,989,952 A 11/1976 Timberlake et al.
(Continued)

FOREIGN PATENT DOCUMENTS

CN 102821918 12/2012
DE 102010040405 3/2012
(Continued)

OTHER PUBLICATIONS

Franzino, "The Laprotek Surgical System and the Next Generation of Robotics," Surg Clin North Am, 2003 83(6): 1317-1320.
(Continued)

*Primary Examiner* — Daniel J Wiley
(74) *Attorney, Agent, or Firm* — Fredrikson & Byron, P.A.; Sean Solberg

(57) ABSTRACT

The various embodiments herein relate to a coupling apparatus for a medical device having a coupler body, a cavity defined in the coupler body, a rotatable drive component disposed within the cavity and having at least two pin-receiving openings, and an actuable locking ring disposed around the cavity.

20 Claims, 5 Drawing Sheets

(51) Int. Cl.
*H01R 24/20* (2011.01)
*H01R 13/24* (2006.01)
*H01R 24/86* (2011.01)
*A61B 17/29* (2006.01)
*H01R 107/00* (2006.01)

(56) References Cited

U.S. PATENT DOCUMENTS

| | | |
|---|---|---|
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,172,639 A | 12/1992 | Wiesman et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Oritz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tiemey et al. |
| 6,346,072 B1 | 2/2002 | Cooper |
| 6,352,503 B1 | 3/2002 | Raifu et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |

(56) References Cited

U.S. PATENT DOCUMENTS

| | | |
|---|---|---|
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,353,897 B2 | 1/2013 | Doyle et al. |
| 9,089,353 B2 | 7/2015 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |

(56) References Cited

U.S. PATENT DOCUMENTS

| | | |
|---|---|---|
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0239311 A1* | 10/2005 | Yokoigawa .......... H01R 13/622 439/311 |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Takumi et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0245549 A1 | 9/2010 | Allen et al. |
| 2010/0262162 A1 | 10/2010 | Omori |
| 2010/0286480 A1 | 11/2010 | Peine et al. |
| 2010/0292691 A1 | 11/2010 | Brogna |
| 2010/0318059 A1 | 12/2010 | Farritor et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |

(56) References Cited

U.S. PATENT DOCUMENTS

| | | |
|---|---|---|
| 2011/0098529 A1 | 4/2011 | Ostrovsky et al. |
| 2011/0132960 A1 | 6/2011 | Whitman et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0253515 A1 | 10/2012 | Coste-Maniere et al. |
| 2013/0131695 A1 | 5/2013 | Scarfogliero et al. |
| 2013/0345717 A1 | 12/2013 | Markvicka et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0249474 A1 | 9/2014 | Suon et al. |
| 2014/0303434 A1 | 10/2014 | Farritor et al. |
| 2014/0373652 A1 | 12/2014 | Zergiebel et al. |
| 2015/0051446 A1 | 2/2015 | Farritor et al. |
| 2016/0143688 A1 | 5/2016 | Orban, III et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| EP | 2684528 A1 | 1/2014 |
| EP | 2815705 A1 | 12/2014 |
| EP | 2881046 A2 | 10/2015 |
| EP | 2937047 A1 | 10/2015 |
| JP | 05-115425 | 5/1993 |
| JP | 2006508049 | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004144533 | 5/2004 |
| JP | 2004-180781 | 7/2004 |
| JP | 2004322310 | 11/2004 |
| JP | 2004329292 | 11/2004 |
| JP | 2006507809 | 3/2006 |
| JP | 2009106606 | 5/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009023851 | 2/2009 |
| WO | 2009144729 | 12/2009 |
| WO | 2010050771 | 5/2010 |
| WO | 2011075693 | 6/2011 |
| WO | 2011118646 | 9/2011 |
| WO | 2011135503 | 11/2011 |
| WO | 2013009887 | 1/2013 |
| WO | 2014011238 | 1/2014 |

OTHER PUBLICATIONS

Franklin et al., "Prospective Comparison of Open vs. Laparoscopic Colon Surgery for Carcinoma: Five-Year Results," Dis Colon Rectum, 1996; 39: S35-S46.

Flynn et al., "Tomorrow's surgery: micromotors and microrobots for minimally invasive procedures," Minimally Invasive Surgery & Allied Technologies, 1998; 7(4): 343-352.

Fireman et al., "Diagnosing small bowel Crohn's desease with wireless capsule endoscopy," Gut 2003; 52: 390-392.

Fearing et al., "Wing Transmission for a Micromechanical Flying Insect," Proceedings of the 2000 IEEE International Conference to Robotics & Automation, Apr. 2000; 1509-1516.

Faraz et al., "Engineering Approaches to Mechanical and Robotic Design for Minimaly Invasive Surgery (MIS)," Kluwer Academic Publishers (Boston), 2000, 13pp.

Falcone et al., "Robotic Surgery," Clin. Obstet. Gynecol. 2003, 46(1): 37-13.

Fraulob et al., "Miniature assistance module for robot-assisted heart surgery," Biomed. Tech. 2002, 47 Suppl. 1, Pt. 1: 12-15.

Fukuda et al., "Mechanism and Swimming Experiment of Micro Mobile Robot in Water," Proceedings of the 1994 EEE International Conference on Robotics and Automation, 1994: 814-819.

Fukuda et al., "Micro Active Catheter System with Multi Degrees of Freedom," Proceedings of the IEEE International Conference on Robotics and Automation, May 1994, pp. 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.

Dumpert et al., "Improving in Vivo Robot Visioin Quality," from the Proceedings of Medicine Meets Virtual Realtiy, Long Beach, CA, Jan. 26-29, 2005. 1 pg.

Dakin et al., "Comparison of laparoscopic skills performance between standard instruments and two surgical robotic systems," Surg Endosc., 2003; 17: 574-579.

Cuschieri, "Technology for Minimal Access Surgery," BMJ, 1999, 319: 1-6.

Grady, "Doctors Try New Surgery for Gallbladder Removal," The New York Times, Apr. 20, 2007, 3 pp.

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.

Chanthasopeephan et al., (2003), "Measuring Forces in Liver Cutting: New Equipment and Experimenal Results," Annals of Biomedical Engineering 31:1372-1382.

Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1):22-29.

Guber et al., "Miniaturized Instrument Systems for Minimally Invasive Diagnosis and Therapy," Biomedizinische Technic 2002, Band 47, Erganmngsband 1: 198-201.

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

Allendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Atmel 80C5X2 Core, http://www.atmel.com, 2006, 186pp.

(56) References Cited

OTHER PUBLICATIONS

Bailey et al., "Complications of Laparoscopic Surgery," Quality Medical Publishers, Inc., 1995, 25pp.

Ballantyne, "Robotic Surgery, Telerobotic Surgery, Telepresence, and Telementoring," Surgical Endoscopy, 2002; 16: 1389-1402.

Bauer et al., "Case Report: Remote Percutaneous Renal Percutaneous Renal Access Using a New Automated Telesurgical Robotic System," Telemedicine Journal and e-Health 2001; (4): 341-347.

Begos et al., "Laparoscopic Cholecystectomy: From Gimmick to Gold Standard," J Clin Gastroenterol, 1994; 19(4): 325-330.

Berg et al., "Surgery with Cooperative Robots," Medicine Meets Virtual Reality, Feb. 2007, 1 pg.

Breda et al., "Future developments and perspectives in laparoscopy," Eur. Urology 2001; 40(1): 84-91.

Breedveld et al., "Design of Steerable Endoscopes to Improve the Visual Perception of Depth During Laparoscopic Surgery," ASME, Jan. 2004; vol. 126, pp. 1-5.

Breedveld et al., "Locomotion through the Intestine by means of Rolling Stents," Proceedings of the ASME Design Engineering Technical Conferences, 2004, pp. 1-7.

Calafiore et al., Multiple Arterial Conduits Without Cardiopulmonary Bypass: Early Angiographic Results,: Ann Thorac Surg, 1999; 67: 450-456.

Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.

Dumpert et al., "Stereoscopic In Vivo Surgical Robots," IEEE Sensors Special Issue on In Vivo Sensors for Medicine, Jan. 2007, 10 pp.

Green, "Telepresence Surgery", Jan. 1, 1995, Publisher: IEEE Engineering in Medicine and Biology.

Cleary et al., "State of the Art in Surgical Rooties: Clinical Applications and Technology Challenges", "Computer Aided Surgery", Jan. 1, 2002, pp. 312-328, vol. 6.

Stoianovici et al., "Robotic Tools for Minimally Invasive Urologic Surgery", Jan. 1, 2002, pp. 1-17.

\* cited by examiner

QUICK-RELEASE END EFFECTOR TOOL INTERFACE

CROSS-REFERENCE TO RELATED APPLICATION(S)

This application claims the benefit under 35 U.S.C. § 119(e) to U.S. Provisional Application 62/379,344, filed Aug. 24, 2016 and entitled "Quick-Release End Effector Tool Coupler," which is hereby incorporated herein by reference in its entirety.

GOVERNMENT SUPPORT

This invention was made with government support under Grant No. W81XWH-14-1-0058, awarded by the U.S. Army Medical Research Acquisition ACT. The government has certain rights in the invention.

FIELD OF THE INVENTION

The various embodiments herein relate to coupling mechanisms that provide for quick coupling to and quick release from a medical device tool such as, for example, an end effector. The various coupling mechanism embodiments can be incorporated into or attached to various types of medical devices, including robotic surgical devices and systems.

BACKGROUND OF THE INVENTION

Many known surgical device systems, including robotic systems, utilize a tool coupler that consists of concentric splines and a quarter-turn system to lock the tool into the front of the device (or an arm thereof). In other words, the coupler requires that the tool be positioned in the coupler on the device and rotated ¼ turn to align the concentric splines and thereby couple or attach the tool to the device. In these known couplers, once the tool is attached to the device, the concentric splines also operate to transfer rotary motion from the device to the tool.

There is a need in the art for an improved end effector tool coupler for use with various types of medical devices.

BRIEF SUMMARY OF THE INVENTION

Discussed herein are various coupling mechanisms, apparatuses, and components for quick-release attachment of various medical tools to various medical devices and systems.

In Example 1, a coupling apparatus for a medical device comprises a coupler body, a cavity defined in a distal end of the coupler body, a rotatable drive component disposed within the cavity, the drive component comprising at least two pin-receiving openings, and an actuable locking ring disposed around the cavity.

Example 2 relates to the coupling apparatus according to Example 1, wherein the coupler body is coupleable to a tool, wherein the tool comprises a tool body sized and arranged to be positionable within the cavity and a rotatable driven component operably coupled to the tool body. The rotatable driven component comprises at least two pin chambers defined in the rotatable driven component, and at least two tensioned pins, wherein each of the at least two tensioned pins is disposed within and is extendable from one of the at least two pin chambers comprising at least two tensioned pins extending therefrom. The rotatable driven component is alignable with the rotatable drive component such that the at least two tensioned pins extend into the at least two pin-receiving openings.

Example 3 relates to the coupling apparatus according to Example 1, wherein the rotatable drive component comprises an inner drive component comprising at least two inner pin-receiving openings, and an outer drive component comprising at least two outer pin-receiving openings.

Example 4 relates to the coupling apparatus according to Example 3, wherein the coupler body is coupleable to a tool, wherein the tool comprises a tool body sized and arranged to be positionable within the cavity, and a rotatable driven component operably coupled to the tool body. The rotatable driven component comprises an inner driven component comprising at least two inner pin chambers defined in the inner driven component and at least two inner tensioned pins disposed within and extendable from the at least two inner pin chambers, and an outer driven component comprising at least two outer pin chambers defined in the outer driven component and at least two outer tensioned pins disposed within and extendable from the at least two outer pin chambers. The inner driven component is alignable with the inner drive component such that the at least two inner tensioned pins extend into the at least two inner pin-receiving openings, and the outer driven component is alignable with the outer drive component such that the at least two outer tensioned pins extend into the at least two outer pin-receiving openings.

Example 5 relates to the coupling apparatus according to Example 3, further comprising an insulation layer disposed between the inner and outer drive components.

Example 6 relates to the coupling apparatus according to Example 1, wherein the actuable locking ring is movable between a depressed position in which any tool body disposed within the cavity is releasable and a non-depressed position in which any tool body disposed within the cavity is locked therein.

Example 7 relates to the coupling apparatus according to Example 1, further comprising an elongate tube disposed through a length of the coupler body such that the rotatable drive component is disposed around a distal portion of the elongate tube, the elongate tube comprising a lumen in fluid communication with a distal opening of the elongate tube.

In Example 8, a coupling system for a medical device comprises a coupling apparatus associated with the medical device and a tool body coupleable with the coupling apparatus. The apparatus comprises a coupler body, a cavity defined in a distal end of the coupler body, a rotatable drive component disposed within the cavity, the drive component comprising at least two pin-receiving openings, and an actuable locking ring disposed around the cavity. The tool body is sized and arranged to be positionable within the cavity and comprises a rotatable driven component operably coupled to the tool body. The rotatable driven component comprises at least two pin chambers defined in the rotatable driven component, and at least two tensioned pins disposed within and extendable from the at least two pin chambers. The rotatable driven component is alignable with the rotatable drive component such that the at least two tensioned pins extend into the at least two pin-receiving openings.

Example 9 relates to the coupling system according to Example 8, wherein the rotatable drive component comprises an inner drive component comprising at least two inner pin-receiving openings, and an outer drive component comprising at least two outer pin-receiving openings.

Example 10 relates to the coupling system according to Example 9, wherein the rotatable driven component comprises a rotatable inner driven component, wherein the at least two pin chambers comprise at least two inner pin chambers defined in the rotatable inner driven component, and wherein the at least two tensioned pins comprise at least two inner tensioned pins disposed within and extendable from the at least two inner pin chambers, and a rotatable outer driven component, wherein the at least two pin chambers comprise at least two outer pin chambers defined in the rotatable outer driven component, and wherein the at least two tensioned pins comprise at least two outer tensioned pins disposed within and extendable from the at least two outer pin chambers. The rotatable inner driven component is alignable with the inner drive component such that the at least two inner tensioned pins extend into the at least two inner pin-receiving openings, and the rotatable outer driven component is alignable with the outer drive component such that the at least two outer tensioned pins extend into the at least two outer pin-receiving openings.

Example 11 relates to the coupling system according to Example 9, further comprising an insulation layer disposed between the inner and outer drive components.

Example 12 relates to the coupling system according to Example 8, wherein the actuable locking ring is movable between a depressed position in which the tool body is releasable from the cavity and a non-depressed position in which the tool body disposed within the cavity is locked therein.

Example 13 relates to the coupling system according to Example 8, further comprising an elongate tube disposed through a length of the coupler body such that the rotatable drive component is disposed around a distal portion of the elongate tube, the elongate tube comprising a lumen in fluid communication with a distal opening of the elongate tube.

In Example 14, a coupling system for a medical device comprises a coupling apparatus associated with the medical device and a tool body coupleable with the coupling apparatus. The coupling apparatus comprises a coupler body, a cavity defined in a distal end of the coupler body, an inner drive component comprising at least two inner pin-receiving openings, an outer drive component comprising at least two outer pin-receiving openings, and an actuable locking ring disposed around the cavity. The tool body is sized and arranged to be positionable within the cavity and comprises a rotatable inner driven component and a rotatable outer driven component. The rotatable inner driven component comprises at least two inner pin chambers defined in the rotatable inner driven component, and at least two inner tensioned pins disposed within and extendable from the at least two inner pin chambers. The rotatable outer driven component comprises at least two outer pin chambers defined in the rotatable outer driven component, and at least two outer tensioned pins disposed within and extendable from the at least two outer pin chambers. The rotatable inner driven component is alignable with the inner drive component such that the at least two inner tensioned pins extend into the at least two inner pin-receiving openings, and the rotatable outer driven component is alignable with the outer drive component such that the at least two outer tensioned pins extend into the at least two outer pin-receiving openings.

Example 15 relates to the coupling system according to Example 14, further comprising an insulation layer disposed between the inner and outer drive components.

Example 16 relates to the coupling system according to Example 14, wherein the actuable locking ring is movable between a depressed position in which the tool body is releasable from the cavity and a non-depressed position in which the tool body disposed within the cavity is locked therein.

Example 17 relates to the coupling system according to Example 14, further comprising an elongate tube disposed through a length of the coupler body such that the rotatable drive component is disposed around a distal portion of the elongate tube, the elongate tube comprising a lumen in fluid communication with a distal opening of the elongate tube.

In Example 18, a method of coupling a tool to a medical device comprises positioning a rotatable driven component of a tool into a cavity of a coupling apparatus, the coupling apparatus comprising a rotatable drive component disposed within the cavity, wherein the rotatable drive component comprises at least two pin-receiving openings, and wherein the rotatable driven component comprises at least two pin chambers and at least two tensioned pins disposed within and extendable from the at least two pin chambers, and urging the rotatable driven component toward the rotatable drive component, whereby the at least two tensioned pins are urged into the at least two pin-receiving openings such that the rotatable drive component and the rotatable driven component are rotatably coupled.

In Example 19, a method of coupling a tool to a medical device comprises positioning a rotatable driven component of a tool into a cavity of a coupling apparatus, the coupling apparatus comprising a rotatable drive component disposed within the cavity, wherein the rotatable drive component comprises at least two pin-receiving openings, and wherein the rotatable driven component comprises at least two pin chambers and at least two tensioned pins disposed within and extendable from the at least two pin chambers, urging the rotatable driven component toward the rotatable drive component, whereby the at least two tensioned pins are urged into contact with the rotatable drive component such that the at least two tensioned pins are urged into the at least two pin chambers, and rotating the rotatable drive component in relation to the rotatable driven component until the at least two pin-receiving openings align with the at least two pin chambers such that the at least two tensioned pins are urged into the at least two pin-receiving openings such that the rotatable drive component and the rotatable driven component are rotatably coupled.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
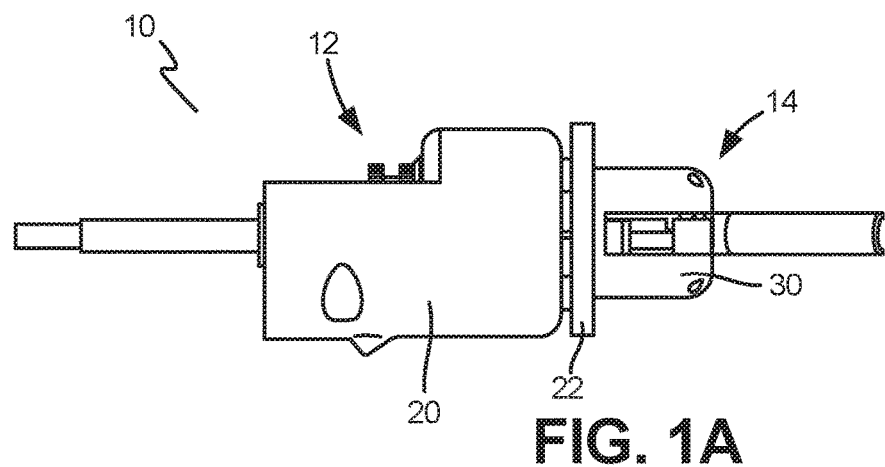
FIG. 1A is a side view of a coupling mechanism coupled to a device tool, according to one embodiment.

The various systems and devices disclosed herein relate to devices for use in medical procedures and systems. More specifically, various embodiments relate to a quick-change coupling apparatus or component that can be used to releasably couple a tool or end effector to a medical device or a component thereof (such as, for example, an arm of the device). For example, in certain implementations, the medical device is a robotic surgical device with an arm having the coupling mechanism disposed on the arm such that one or more end effectors can be coupled to and detached from the arm via the coupling mechanism.

Rather than the known quarter-turn configuration as discussed above, the implementations disclosed or contemplated herein relate to a self-locking quick release mechanism that includes a spring-loaded coupling component (also referred to herein as an "coupler" or "coupler) (rather than concentric splines) that provides for a compliant passage of actuation forces without requiring any type of alignment step during the process of coupling the tool to the coupling component.

The various systems and devices disclosed herein relate to devices, or components thereof, for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in U.S. Pat. No. 8,968,332 (issued on Mar. 3, 2015 and entitled "Magnetically Coupleable Robotic Devices and Related Methods"), U.S. Pat. No. 8,834,488 (issued on Sep. 16, 2014 and entitled "Magnetically Coupleable Surgical Robotic Devices and Related Methods"), U.S. patent application Ser. No. 14/617,232 (filed on Feb. 9, 2015 and entitled "Robotic Surgical Devices and Related Methods"), U.S. Pat. No. 9,579,088 (issued on Feb. 28, 2017 and entitled "Methods, Systems, and Devices for Surgical Visualization and Device Manipulation"), U.S. Pat. No. 8,343,171 (issued on Jan. 1, 2013 and entitled "Methods and Systems of Actuation in Robotic Devices"), U.S. Pat. No. 8,828,024 (issued on Sep. 9, 2014 and entitled "Methods and Systems of Actuation in Robotic Devices"), U.S. patent application Ser. No. 14/454,035 (filed Aug. 7, 2014 and entitled "Methods and Systems of Actuation in Robotic Devices"), U.S. patent application Ser. No. 12/192,663 (filed Aug. 15, 2008 and entitled Medical Inflation, Attachment, and Delivery Devices and Related Methods"), U.S. patent application Ser. No. 15/018,530 (filed Feb. 8, 2016 and entitled "Medical Inflation, Attachment, and Delivery Devices and Related Methods"), U.S. Pat. No. 8,974,440 (issued on Mar. 10, 2015 and entitled "Modular and Cooperative Medical Devices and Related Systems and Methods"), U.S. Pat. No. 8,679,096 (issued on Mar. 25, 2014 and entitled "Multifunctional Operational Component for Robotic Devices"), U.S. Pat. No. 9,179,981 (issued on Nov. 10, 2015 and entitled "Multifunctional Operational Component for Robotic Devices"), U.S. patent application Ser. No. 14/936,234 (filed on Nov. 9, 2015 and entitled "Multifunctional Operational Component for Robotic Devices"), U.S. Pat. No. 8,894,633 (issued on Nov. 25, 2014 and entitled "Modular and Cooperative Medical Devices and Related Systems and Methods"), U.S. Pat. No. 8,968,267 (issued on Mar. 3, 2015 and entitled "Methods and Systems for Handling or Delivering Materials for Natural Orifice Surgery"), U.S. Pat. No. 9,060,781 (issued on Jun. 23, 2015 and entitled "Methods, Systems, and Devices Relating to Surgical End Effectors"), U.S. patent application Ser. No. 14/745,487 (filed on Jun. 22, 2015 and entitled "Methods, Systems, and Devices Relating to Surgical End Effectors"), U.S. Pat. No. 9,089,353 (issued on Jul. 28, 2015 and entitled "Robotic Surgical Devices, Systems, and Related Methods"), U.S. patent application Ser. No. 14/800,423 (filed on Jul. 15, 2015 and entitled "Robotic Surgical Devices, Systems, and Related Methods"), U.S. patent application Ser. No. 13/573,849 (filed Oct. 9, 2012 and entitled "Robotic Surgical Devices, Systems, and Related Methods"), U.S. patent application Ser. No. 13/738,706 (filed Jan. 10, 2013 and entitled "Methods, Systems, and Devices for Surgical Access and Insertion"), U.S. patent application Ser. No. 13/833,605 (filed Mar. 15, 2013 and entitled "Robotic Surgical Devices, Systems, and Related Methods"), U.S. patent application Ser. No. 14/661,465 (filed Mar. 18, 2015 and entitled "Methods, Systems, and Devices for Surgical Access and Insertion"), U.S. Pat. No. 9,498,292 (issued on Nov. 22, 2016 and entitled "Single Site Robotic Devices and Related Systems and Methods"), U.S. patent application Ser. No. 15/357,663 (filed Nov. 21, 2016 and entitled "Single Site Robotic Devices and Related Systems and Methods"), U.S. Pat. No. 9,010,214 (issued on Apr. 21, 2015 and entitled "Local Control Robotic Surgical Devices and Related Methods"), U.S. patent application Ser. No. 14/656,109 (filed on Mar. 12, 2015 and entitled "Local Control Robotic Surgical Devices and Related Methods"), U.S. patent application Ser. No. 14/208,515 (filed Mar. 13, 2014 and entitled "Methods, Systems, and Devices Relating to Robotic Surgical Devices, End Effectors, and Controllers"), U.S. patent application Ser. No. 14/210,934 (filed Mar. 14, 2014 and entitled "Methods, Systems, and Devices Relating to Force Control Surgical Systems), U.S. patent application Ser. No. 14/212,686 (filed Mar. 14, 2014 and entitled "Robotic Surgical Devices, Systems, and Related Methods"), U.S. patent application Ser. No. 14/334,383 (filed Jul. 17, 2014 and entitled "Robotic Surgical Devices, Systems, and Related Methods"), U.S. patent application Ser. No. 14/853,477 (filed Sep. 14, 2015 and entitled "Quick-Release End Effectors and Related Systems and Methods"), U.S. patent application Ser. No. 14/938,667 (filed Nov. 11, 2015 and entitled "Robotic Device with Compact Joint Design and Related Systems and Methods"), U.S. patent application Ser. No. 15/227,813 (filed Aug. 3, 2016 and entitled "Robotic Surgical Devices, Systems, and Related Methods"), U.S. patent application Ser. No. 15/599,231 (filed May 18, 2017 and entitled "Robotic Surgical Devices, Systems, and Related Methods"), U.S. Patent Application 62/381,299 (filed Aug.

30, 2016 and entitled "Robotic Device with Compact Joint Design and an Additional Degree of Freedom and Related Systems and Methods"), U.S. Patent Application 62/425,149 (filed Nov. 22, 2016 and entitled "Improved Gross Positioning Device and Related Systems and Methods"), U.S. Patent Application 62/427,357 (filed Nov. 29, 2016 and entitled "Controller with User Presence Detection and Related Systems and Methods"), U.S. Patent Application 62/433,837 (filed Dec. 14, 2016 and entitled "Releasable Attachment Device for Coupling to Medical Devices and Related Systems and Methods"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

Figure 1B:
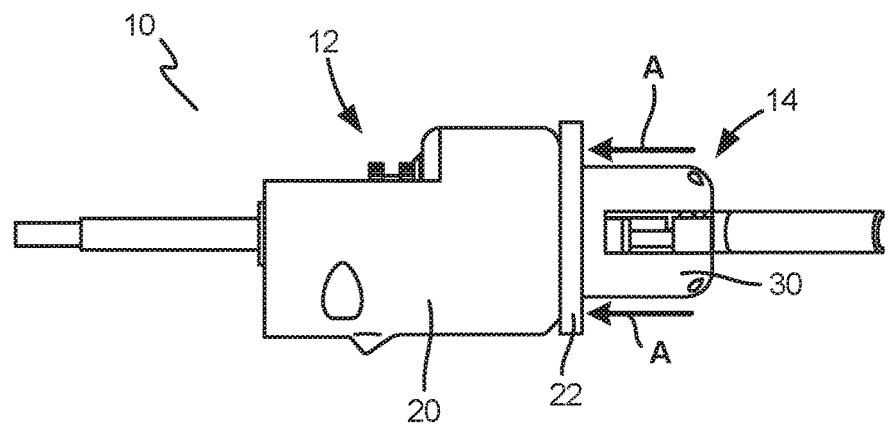
FIG. 1B is a side view of the coupling mechanism and device tool of FIG. 1A in which the locking mechanism has been depressed, according to one embodiment.
Figure 1C:
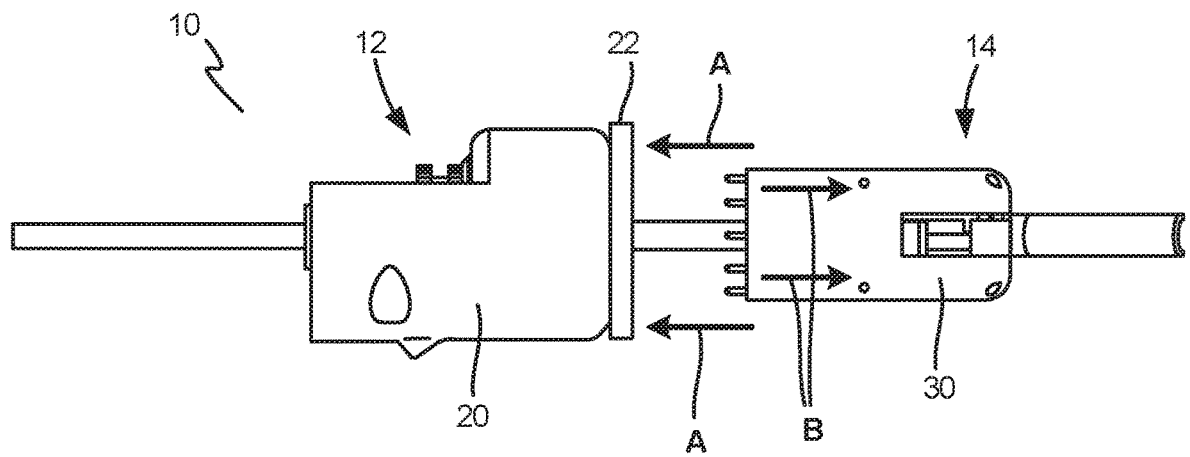
FIG. 1C is a side view of the coupling mechanism and device tool of FIG. 1A in which the device tool is being uncoupled from the coupling mechanism, according to one embodiment.

FIGS. 1A-1C depict one embodiment of a self-locking quick release mechanism 10 for coupling a device tool 14 to a coupler 12. It is understood that the coupler 12 is coupled to or integral with a medical device or some component thereof, such that the coupling of a device tool 14 to the coupler 12 results in the device tool 14 being coupled to the medical device. For example, in certain implementations, the coupler 12 is coupled to or integral with a distal end of a robotic arm of the medical device. In more specific implementations, the coupler 12 is coupled to or integral with a distal end of a forearm of a robotic arm of the medical device. The coupler 12 has a coupler body 20 and an actuable locking ring 22. The actuable locking ring 22 can be depressed (or urged proximally toward the coupler body 20) as shown by the arrows A in FIG. 1B to trigger the release of the device tool 14 from the coupler 12.

The removable device tool 14, according to some implementations, is an end effector 14 for coupling to an arm of a medical device via the coupler 12. Alternatively, the end effector 14 is being coupled to a distal end of a forearm of a medical device via the coupler 12. The removable device tool 14 can have any number of different configurations or can be any one of several different types of tools. Regardless of the configuration of the tool 14, it has a tool body 30 that is configured to be positionable in and coupleable with the coupler body 20.

In use, the tool 14 can be removed or uncoupled from the coupler 12 by urging the actuable locking ring 22 proximally toward the coupler body 20 as shown in FIG. 1B, thereby releasing the tool 14 such that it can be urged distally as shown via the arrows B in FIG. 1C and removed from the coupler 12. It is understood that after the tool 14 has been removed, the tool 14 can be re-attached to the coupler 12—or another tool 14 can be attached thereto—by simply urging the tool 14 proximally into the locking ring 22 such that the tool 14 couples to the coupler 12.

One exemplary tool 50 that is coupleable to a coupler (such as coupler 12 discussed above) is depicted in FIGS. 2A and 2B and has an end effector body 52. As best shown in FIG. 2B, the proximal end of the end effector body 52 has pins (also referred to herein as "tensioned pins" or "spring-loaded pins") 58A, 58B disposed within and extending from the proximal end 54 of the body 52 in their resting state. Each of the pins 58A, 58B is disposed within an opening (also referred to herein as a "pin chamber") 56A, 56B defined in the proximal end 54 such that each pin 58A, 58B can be urged toward the body 52 into its chamber 56A, 56B. That is, each pin 58A, 58B is coupled to a force mechanism (not shown) that has a resting state in which the pin 58A, 58B is extended from the pin chamber 56A, 56B and applies a force to the pin 58A, 58B when the pin 58A, 58B is urged toward the end effector body 52. In one embodiment, the force mechanism is a compression spring (not shown). Alternatively, any known force mechanism that operates as described can be used.

In the exemplary embodiment as shown, the end effector body 52 has eight spring-loaded pins 58A, 58B, with four pins 58A disposed in four pin chambers 56A defined in an inner driven component 60A and four pins 58B disposed in four pin chambers 56B defined in an outer driven component 60B, wherein the two driven components 60A, 60B are concentric or coaxial. That is, the two driven components 60A, 60B are separate components that rotate around the same axis. Alternatively, the body 52 can have a number of pins ranging from one pin to any number of pins that can be disposed in chambers on the proximal end 54 of the body 52. In one specific alternative embodiment, the proximal end 54 has at least four pins disposed in four pin chambers. In a further alternative, the proximal end 54 has at least two pins disposed in two pin chambers.

In this specific implementation, the end effector body 52 also has a central tube 70 disposed therethrough that defines a central lumen 72 within the tube 70. The central tube 70 can be used in several different capacities, thereby making it possible for the tool 50 to be one of several different types of tools. That is, the tube 70 with its central lumen 72 can be used for suction, irrigation, tool delivery, drug delivery, clip application, and/or biopsy collection, and various other known features of various medical device tools or end effectors.

Alternatively, there are tool configurations that don't require a tube 70 with a lumen 72, and thus the body 52 according to certain implementations can have no tube. Without the tube 70, the body 52 can have a smaller diameter. In one specific embodiment in which the body 52 has no tube, the body can have a diameter of around ⅜ inch, thereby allowing the end effector 50 to fit through a standard laparoscopic port (which has an inner diameter of around 10 mm.

In one implementation, the coaxial driven components 60A, 60B can rotate in relation to each other, thereby adding an additional degree of freedom to the tool 50. In alternative embodiments, the body 52 doesn't have two concentric driven components, but instead the body 52 is a single, unitary component.

Figure 2A:
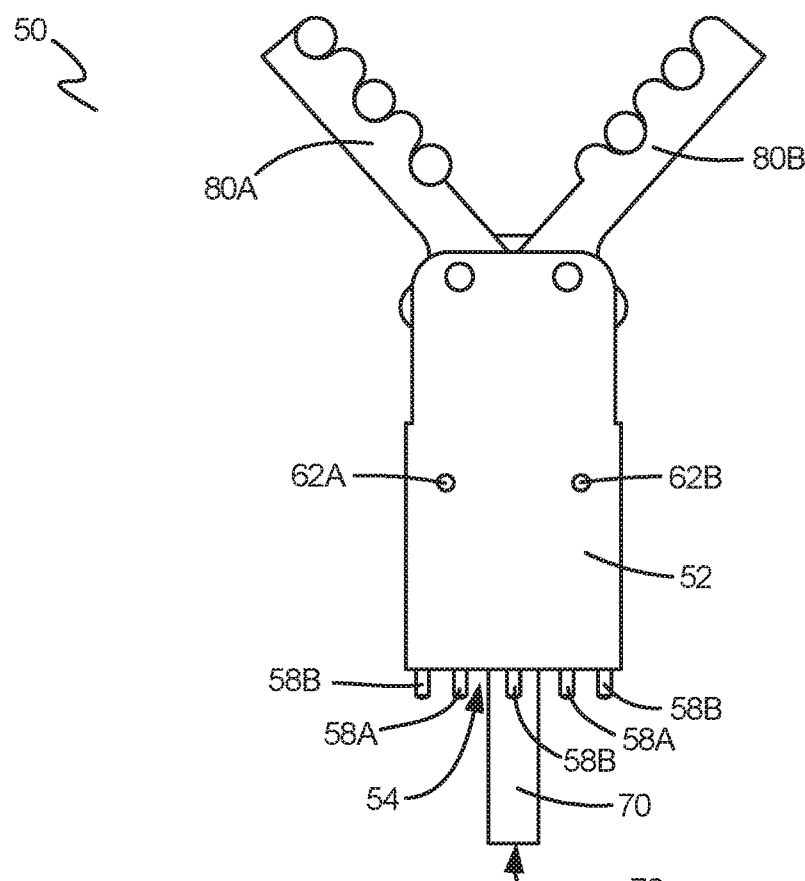
FIG. 2A is a side view of a graspers end effector, according to one embodiment.
Figure 2B:
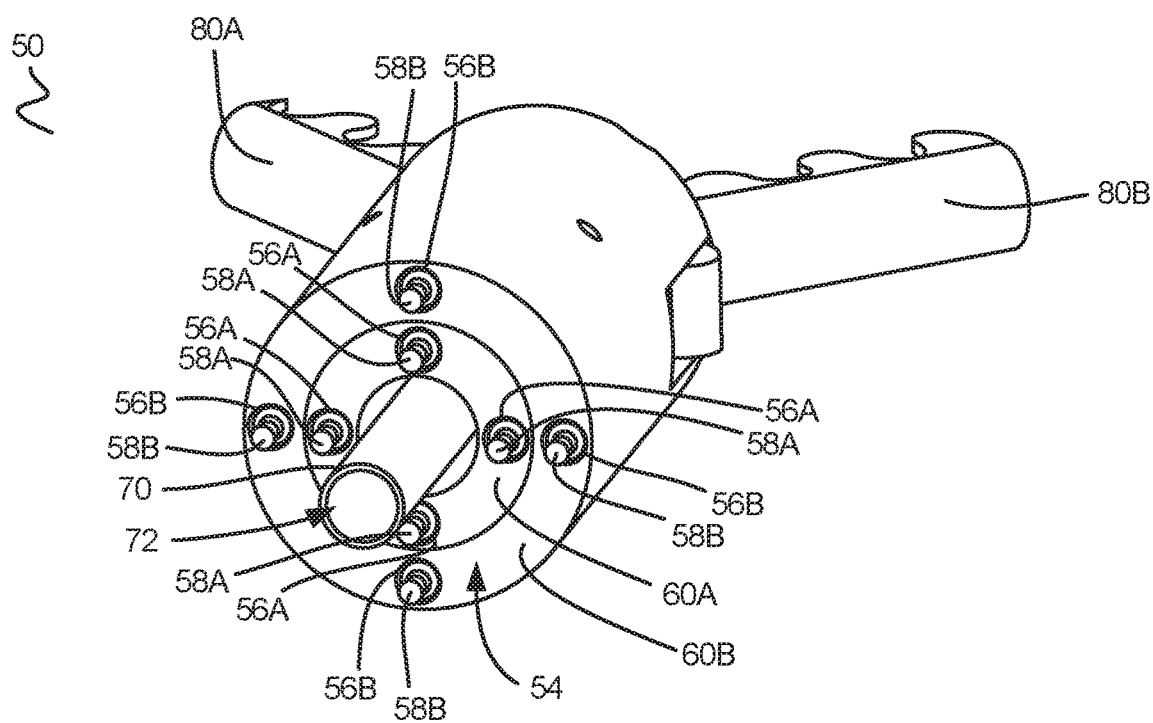
FIG. 2B is a perspective rear view of the graspers end effector of FIG. 2A.

In the exemplary embodiment as shown in FIGS. 2A and 2B, the tool 50 is a set of graspers 50. That is, the graspers end effector 50 has two grasper arms 80A, 80B coupled to the end effector body 52.

Figure 3:
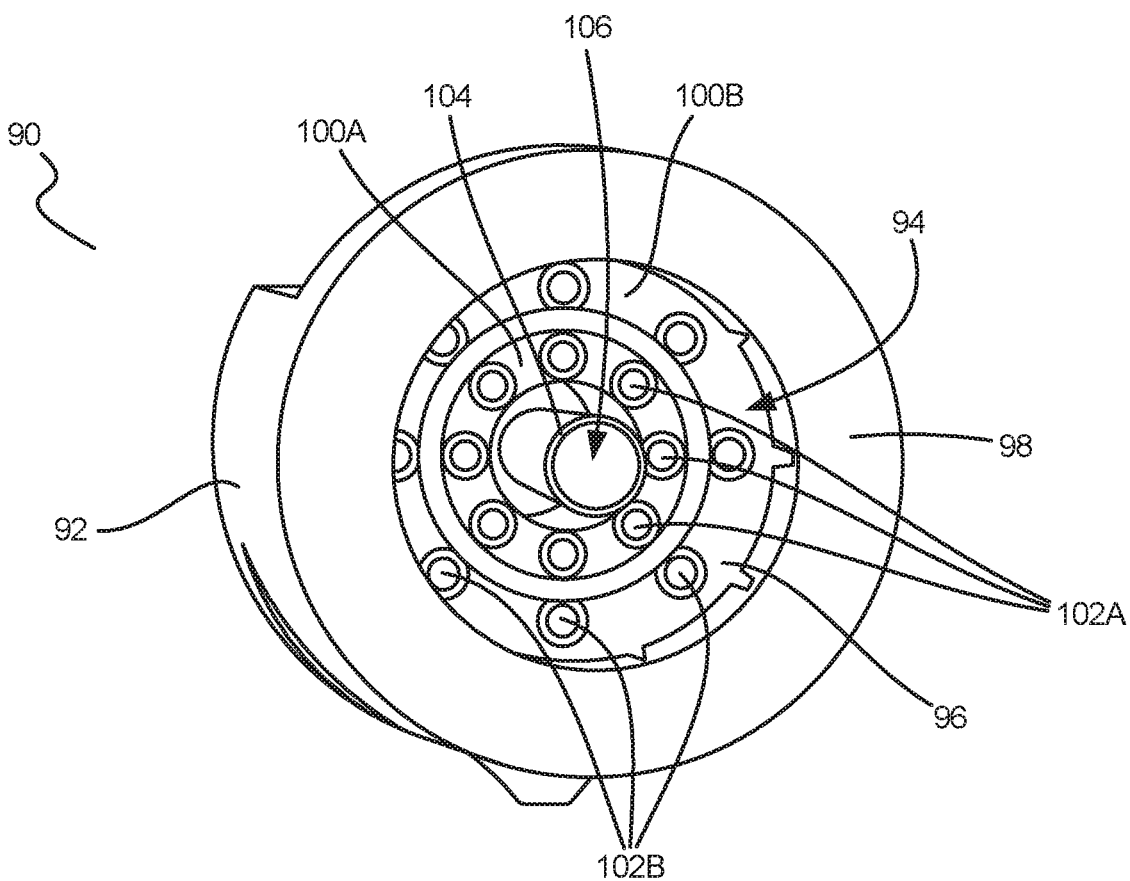
FIG. 3 is a perspective front view of a coupling mechanism, according to another embodiment.

The spring-loaded pins 58A, 58B on the tool 50 as described above are configured to operate in conjunction with a corresponding device coupler (such as the coupler 12 discussed above, for example, or any other coupler embodiment disclosed or contemplated herein) to allow for the coupling of the tool 50 to the coupler without the need for an alignment step. This non-alignment coupling is best described in relation to the coupler to which the body 50 is coupled. One example of a device coupler 90 is depicted in FIG. 3 according to one implementation, in which the coupler 90 has a coupler body 92, a coupler cavity 94, a coupler drive component 96 disposed within the cavity 94, and an actuable locking ring 98 disposed around the cavity 94. In this specific implementation, the coupler drive component 96 is actually made up of two drive components: a first or inner drive component 100A and a second or outer drive component 100B, wherein the drive components 100A, 100B are coaxial and rotatable in relation to each other. Further, each of the drive components 100A, 100B has pin-receiving openings 102A, 102B defined therein. More specifically, in this particular embodiment, the inner drive component 100A has eight openings 102A and the outer drive component 100B has eight openings 102B. The eight openings 102A defined in the inner drive component 100A are configured to receive the spring-loaded pins of an inner driven component of a proximal end of a coupleable tool (such as the pins 58A of the inner driven component 60A of the tool 50 discussed above, for example), while the eight openings 102B defined in the outer drive component 100B are configured to receive the spring-loaded pins of an outer driven component of a proximal end of a coupleable tool (such as the pins 58B of the outer driven component 60B of the tool 50 discussed above, for example). Alternatively, the coupler drive component 96 doesn't have two concentric drive components and instead has a single, unitary component and thus is configured to couple with the proximal end of a coupleable tool that also has a single, unitary component.

These openings 102A, 102B are defined in a predetermined pattern on the drive component 96 such that the pins 58A, 58B can fit into the openings 102A, 102B. In this embodiment, the inner drive component 100A has twice as many openings 102A as the number of pins 58A on the inner driven component 60A of the tool 50 and the outer drive component 100B has twice as many openings 102B as the number of pins 58B on the outer driven component 60B of the tool 50. As such, the pins 58A, 58B can be positioned in the openings 102A, 102B in two different couplings (in two different sets of the openings 102A, 102B). As such, the fact that there are twice as many openings 102A, 102B as pins 58A, 58B further reduces the coupling time, as will be described in additional detail below.

In addition, this coupler 90 embodiment has a central tube 104 with a lumen 106 that is coupleable to any central tube of the tool to be coupled thereto (such as the tube 70 of the tool 50 described above). Alternatively, the coupler 90 does not have a central tube 104 when the tool to be coupled thereto has no central tube.

In use in which the tool 50 is coupled to the coupler 90, the proximal end 54 of the tool body 52 is inserted into the coupler cavity 90 and urged proximally toward the coupler drive component 96. While it is unlikely, if the pins 58A, 58B happen to be aligned correctly with the openings 102A, 102B without any rotation of either the tool 50 or the coupler 90 in relation to each other, the pins 58A, 58B will be urged into the openings 102A, 102B and disposed therein such that rotation of the inner drive component 100A of the coupler drive component 96 will cause rotation of the inner driven component 60A of the tool 50 and rotation of the outer drive component 100B of the drive component 96 will cause rotation of the outer driven component 60B of the tool 50. In the more likely scenario that the pins 58A, 58B are not aligned correctly with the openings 102A, 102B, the pins 58A, 58B will make contact with the drive component 96 such that the pins 58A, 58B will be urged toward the device body 52 such that the pins 58A, 58B will be urged into their pin chambers 56A, 56B until the proximal end 54 contacts the coupler drive component 96. At this point, the two drive components 100A, 100B of the drive component 96 are rotated in relation to the tool body 52 until the openings 102A, 102B are aligned correctly with the pins 58A, 58B. When the alignment is correct, the force mechanisms (not shown) coupled to each of the pins 58A, 58B will urge the pins proximally toward the coupler body 92, thereby causing the pins 58A, 58B to be positioned in the openings 102A, 102B. Once the pins 58A, 58B are positioned correctly in the openings 102A, 102B, rotation of the inner drive component 100A of the coupler drive component 96 will cause rotation of the inner driven component 60A of the tool 50 and rotation of the outer drive component 100B of the drive component 96 will cause rotation of the outer driven component 60B of the tool 50.

In accordance with one implementation, the coupler 90 having a drive component 96 with openings 102A, 102B makes it easier to sterilize the coupler 90 in comparison to pins (such as pins 58A, 58B), which can be more difficult to sterilize given the additional moving components, relative inaccessibility of some of those components, and related amount of surface area. However, in an alternative embodiment, the coupler (such as coupler 90) could have spring-loaded pins and the tool (such as tool 50) could have openings configured to receive those pins.

Figure 4A:
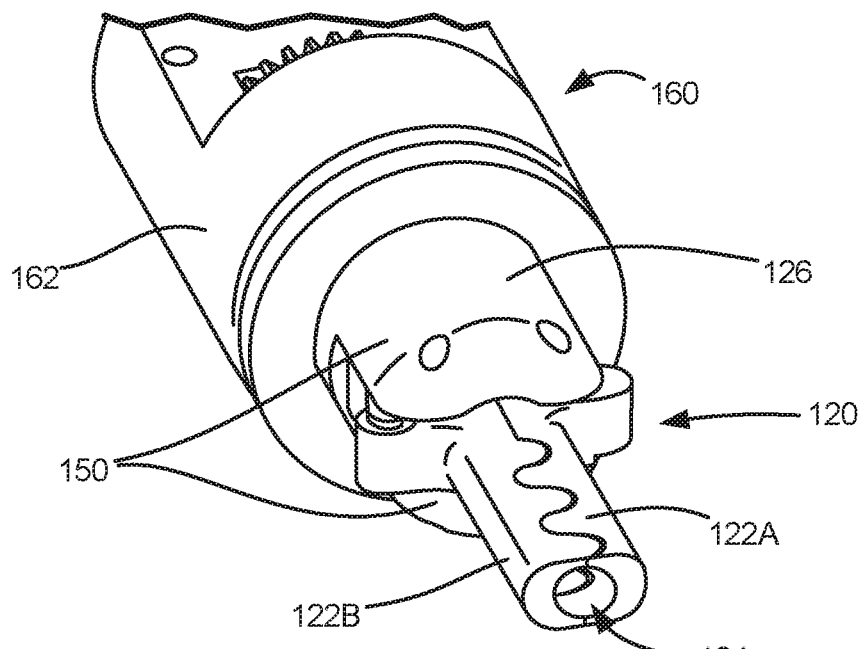
FIG. 4A is a perspective front view of a graspers end effector, according to another embodiment.
Figure 4B:
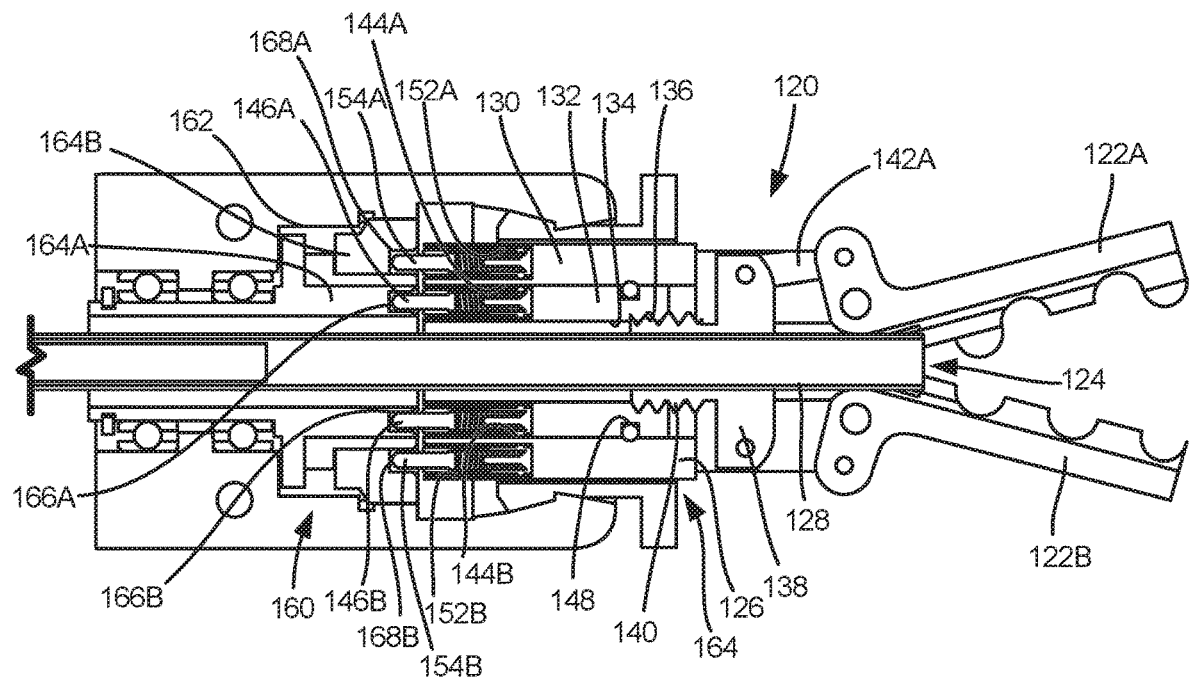
FIG. 4B is a side cutaway view of the graspers end effector of FIG. 4A coupled to a coupling mechanism, according to one embodiment.

FIGS. 4A and 4B depict another device tool 120 that is a graspers tool 120 with suction and irrigation features and is coupled to a coupler 160. More specifically, the tool body 126 is disposed within the cavity (not shown) of the coupler 160. In this embodiment, the device tool 120 is an end effector 120 and the coupler 160 is coupled to or integral with the arm of a robotic device (not shown). The tool 120 has first and second grasper arms 122A, 122B that are configured to form the distal end of a lumen 124 when the two arms 122A, 122B are in their closed position as best shown in FIG. 4A. As best shown in FIG. 4B, the lumen 124 extends from the grasper arms 122A, 122B to the proximal end of the tool body 126 through a central tube 128. The tube 128 is configured to transport irrigation fluid distally to the distal end of the tool 120 and apply suction proximally toward the proximal end of the body 126 through the lumen 124.

As best shown in FIG. 4B, the tool body 126 is made up of an outer driven component 130 and an inner driven component 132 having an inner lumen 134 with threads 136. The tool 120 also has a push rod 138 that is disposed within the inner lumen 134 and extends distally from the lumen 134. The push rod 138 has external threads 140 that mate with the threads 136 of the inner driven component 132. In addition, the rod 138 is coupled at its distal end to the arm links 142A, 142B (wherein only the arm link 142A is depicted in FIG. 4B) that are coupled to the grasper arms 122A, 122B such that actuation of the push rod 138 causes actuation of the arms 122A, 122B to move between their open and closed configurations. The proximal end of the inner driven component 132 has two pin chambers 144A, 144B defined therein such that each chamber 144A, 144B contains a spring-loaded pin 146A, 146B that is configured to be extendable from the chamber 144A, 144B in the manner discussed above with respect to spring-loaded pins 58A, 58B. While two pin chambers 144A, 144B are depicted, it is understand that the inner driven component 132 can have additional chambers that are not visible in the cross-sectional view depicted in FIG. 4B. As such, the inner driven component 132 can have a similar number of chambers as the inner driven component 60A of the tool body 52 described above and shown in FIG. 2B. In addition, the inner driven component 132 in this embodiment has an external channel 148 defined around an outer surface of the component 132. The channel 148 is configured to receive two cylindrical pins (not shown) that are inserted through openings in the tool body 126 similar to the pins 62A, 62B positioned in the tool body 52 as shown in FIG. 2A. These pins prevent the inner driven component 132 from moving laterally while allowing the component 132 to rotate.

The outer driven component 130 is rotatably disposed around the inner driven component 132 as best shown in FIG. 4B and rotationally coupled to (or integral with) the yoke 150 as best shown in FIG. 4A such that rotation of the outer driven component 130 causes rotation of the yoke 150, thereby rotating the grasper arms 122A, 122B. The proximal end of the outer driven component 130 has two pin chambers 152A, 152B defined therein such that each chamber 152A, 152B contains a spring-loaded pin 154A, 154B that is configured to be extendable from the chamber 152A, 152B in the manner discussed above with respect to spring-loaded pins 58A, 58B. While two pin chambers 152A, 152B (and pins 154A, 154B) are depicted, it is understood that the outer driven component 130 can have additional chambers that are not visible in the cross-sectional view depicted in FIG. 4B. As such, the outer driven component 130 can have a similar number of chambers (and pins) as the outer driven component 60B of the tool body 52 described above and shown in FIG. 2B.

As best shown in FIG. 4B, in accordance with one embodiment, the coupler 160 has a coupler body 162 that contains the coupler drive component 164. In this specific implementation, the coupler drive component 164 is made up of the inner drive component 164A and the outer drive component 164B. The inner drive component 164A as shown has two pin-receiving openings 166A, 166B, each of which is configured to receive a corresponding spring-loaded pin as a result of the coupling action described above. More specifically, as shown in FIG. 4B, pin 146A is disposed in opening 166A and pin 146B is disposed in opening 166B. While two openings 166A, 166B are depicted, it is understood that the inner drive component 164A can have additional openings that are not visible in the cross-sectional view depicted in FIG. 4B. As such, the inner drive component 164A can have a similar number of openings as the inner drive component 100A of the coupler drive component 96 described above and shown in FIG. 3.

Further, the outer drive component 164B as shown has two pin-receiving openings 168A, 168B, each of which is configured to receive a corresponding spring-loaded pin as a result of the coupling action described above. More specifically, as shown in FIG. 4B, pin 154A is disposed in opening 168A and pin 154B is disposed in opening 168B. While two openings 168A, 168B are depicted, it is understood that the outer drive component 164B can have additional openings that are not visible in the cross-sectional view depicted in FIG. 4B. As such, the outer drive component 164B can have a similar number of openings as the outer drive component 100B of the coupler drive component 96 described above and shown in FIG. 3.

In use, the inner drive component 164A of the coupler 160 can be actuated to rotate. With the spring-loaded pins (including pins 146A, 146B) of the tool 120 disposed within the pin-receiving openings 166A, 166B of the inner drive component 164A, the rotation of the inner drive component 164A causes the inner driven component 132 to rotate. Because the internal threads 136 of the inner driven component 132 are mated with the external threads 140 of the push rod 138, the rotation of the inner driven component 132 causes the push rod 138 to move laterally. Because the grasper arm 122A, 122B are coupled to the push rod 138 via the links 142A, 142B (wherein only 142A is depicted in FIG. 4B), the lateral movement of the push rod 138 causes the grasper arms 122A, 122B to move between their open and closed configurations.

Further, the outer drive component 164B can also be actuated to rotate. With the spring-loaded pins (including pins 154A, 154B) of the tool 120 disposed within the pin-receiving openings 168A, 168B of the outer drive component 164B, the rotation of the outer drive component 164B causes the outer driven component 130 to rotate. Because the yoke 150 is coupled to or integral with the distal end of the outer driven component 130 (as best shown in FIG. 4A), the rotation of the outer driven component 130 causes the yoke 150 to rotate. Because the grasper arms 122A, 122B are disposed at least partially within the yoke 150 and are rotationally constrained by the yoke 150, the rotation of the yoke 150 causes the grasper arms 122A, 122B to rotate around the same axis.

Figure 5A:
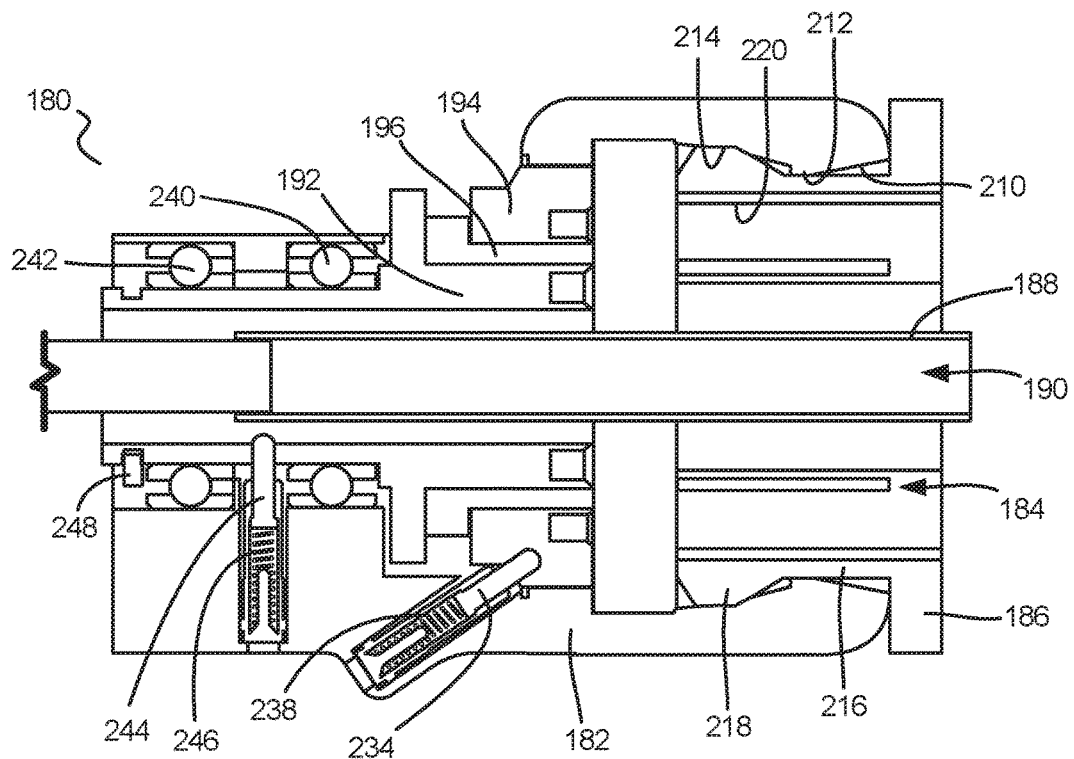
FIG. 5A is a side cutaway view of a coupling mechanism, according to one embodiment.
Figure 5B:
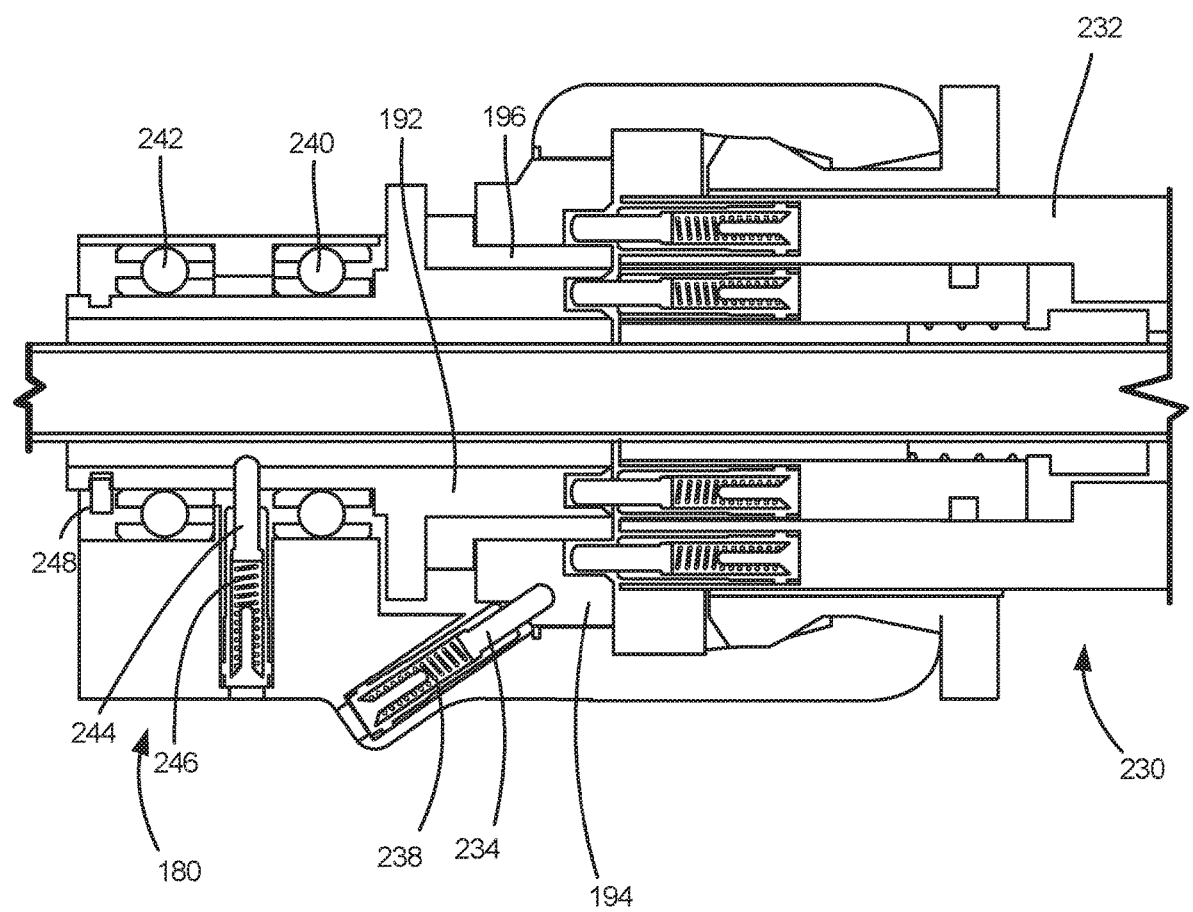
FIG. 5B is a side cutaway view of the coupling mechanism of FIG. 5A coupled to a device tool, according to one embodiment.

FIGS. 5A and 5B depict another embodiment of a coupler 180 coupled to a tool 230, wherein the coupler 180 and tool 230 are configured such that the tool 230 can have bipolar capabilities as will be described below. FIG. 5A depicts the coupler 180 without the tool 230 coupled thereto, while FIG. 5B depicts the coupler 180 and tool 230 coupled together. In this implementation, the coupler 180 and the tool 230 have components and features substantially similar to those described above and depicted in FIGS. 4A and 4B with respect to the coupler 160 and tool 120, except for those differences described herein.

In this embodiment, the coupler 180 is coupled to or integral with the distal end of a forearm of a robotic surgical device (not shown). Alternatively, the coupler 180 can be coupled to or integral with any medical device to which a tool (such as tool 230) is to be coupled. The coupler 180 has a coupler body 182 that has an actuable locking ring 186 disposed within the coupler cavity 184. Further, the body 182 has a central tube 188 that defines a central lumen 190, an inner drive component 192, an outer drive component 194, and an insulation layer 196 disposed between the inner and outer drive components 192, 194, thereby electrically separating the inner and outer drive components 192, 194 to provide for potential bipolar capabilities.

The actuable locking ring 186 can be used to retain or lock the tool 230 in place in the coupler 180 in the following manner. The cavity 184 in this implementation has a narrow portion (or "wall protrusion") 212 defined in the inner wall 210 of the cavity 184. Further, the inner wall 210 also has a wider portion (or "channel") 214 defined in the inner wall proximal to the wall protrusion 212. The actuable locking ring 186 has a corresponding external ring protrusion (also referred to herein as a "fin") 218 extending from an outer wall 216 of the ring 186. In certain embodiments, as the actuable locking ring 186 is moved laterally within the cavity 184, the position of the ring fin 218 in relation to the inner wall channel 214 and the wall protrusion 212 can directly influence the inner diameter of the ring 186. That is, if the ring 186 is disposed within the cavity 184 such that the fin 218 is disposed in the channel 214, the ring 186 has a relatively larger inner diameter. However, if the ring 186 is moved distally within the cavity 184 such that the fin 218 is moved toward the wall protrusion 212, the fin 218 will be urged radially inward, thereby causing the inner diameter of the ring 186 to become smaller. As such, the interaction between the locking ring 186 and the inner wall of the cavity 184 when the locking ring 186 is moved between a locked and an unlocked position causes the inner diameter of the locking ring 186 to be altered, thereby either increasing or reducing the contact friction between the inner wall 220 of the ring 186 and any tool body (such as tool body 232) disposed therein.

Further, the actuable locking ring 186 can also have coupling blades (not shown) disposed along the inner wall 220 of the ring 186 that are configured to enhance the retention of the tool body within the cavity 184 when the inner wall 220 is in contact with the tool body 232. Alternatively, any component or feature can be used that can help to maintain the physical coupling or frictional retention between the inner wall 220 of the ring 186 and the tool body 232.

In use according to one embodiment as best shown in FIG. 1A-1C in combination with FIGS. 5A and 5B, when the locking ring (such as ring 186) is in the locked position as best shown with locking ring 22 in FIG. 1A, the ring fin 218 is disposed adjacent to and in contact with the wall protrusion 212, thereby resulting in a smaller inner diameter of the ring 186 and thus increased contact between the inner wall 220 of the ring 186 and the tool body (such as tool body 30 or tool body 232) disposed therein. This increased contact, along with any retention feature on the inner wall 220 (such as, for example, the retention blades discussed above), results in the tool body (such as body 30 or body 232) being locked or otherwise retained in the coupler 180 (or coupler 12) by the locking ring 186 (or ring 22). Further, as a result of the configuration of the inner wall 210 of the cavity 184 and the configuration of the ring 186, any distal force applied to the tool body 30, 180 will also urge the ring 186 distally as a result of the contact friction between the body 30, 180 and the ring 186, thereby increasing the contact friction between the ring 186 and the body 30, 180. That is, the configuration of the cavity 184 and ring 186 is such that any distal force applied to the tool body 30, 180 actually increases the strength of the locking mechanism.

When the locking ring (such as ring 186) is urged into the unlocked position as best shown in FIGS. 1B and 1C (with respect to ring 22) and FIGS. 5A and 5B (with respect to ring 186, the ring fin 218 is disposed in the channel 214, thereby resulting in a larger inner diameter of the ring 186 (by comparison with the ring 186 in the locked position) and thus decreased (or no) contact between the inner wall 220 of the ring 186 and the tool body (such as tool body 30 or tool body 232) disposed therein. This reduction or elimination of contact results in the tool body (such as body 30 or body 232) being removable from the coupler 180 (or coupler 12).

In this embodiment as shown in FIGS. 5A and 5B, the outer drive component 194 is supplied with an electrical connection via a first electrical contact (also called a "spring pin") 234 that is configured to maintain contact with the drive component 194 while the component 194 is rotating. That is, the spring pin 234 is positioned in the coupler 180 such that it remains in contact with the drive component 194 even when the drive component 194 is actuated to rotate. Further, the spring pin 234 has a force mechanism 238—in this case, a compression spring—that urges the spring pin 234 toward the drive component 194, thereby further ensuring that contact is maintained.

The insulation layer 196 is positioned between the inner drive component 192 and the outer drive component 194 such that the insulation layer 196 electrically isolates the two drive components 192, 194 from each other. The electrical isolation results in two independent electrical conduction paths to any tool (such as tool 230) coupled to the coupler 180 for potential bipolar capability.

According to the embodiment depicted, the inner drive component 192 is supported by two bearings 240, 242. Further, the coupler 180 has a second electrical contact (also called a "spring pin") 244 disposed between the two bearings 240, 242 that is in contact with the inner drive component 192. The second spring pin 244 has a force mechanism 246—in this case, a compression spring—that urges the spring pin 244 toward the drive component 192, thereby further ensuring that contact is maintained. As such, the second spring pin 244 provides the second independent electrical source for the tool (such as tool 230) coupled to the coupler 180. Further, the coupler 180 also has a retaining ring 248 that is positioned in the coupler 180 such that it constrains the inner drive component 192 from translating laterally.

In this implementation, the central tube 188 can be used for suction/irrigation, drug delivery, tool delivery, clip application, and/or other known functions or procedures.

In alternative embodiments, the coupler can provide only one electrical connection (instead of two), thereby eliminating the need for electrical isolation and insulation between components. In further alternatives, the coupler can have three or more electrical connections to provide three or more separate, independent electrical sources for three different uses in the tool (such as tool 230).

The coupler embodiments discussed above have included two drive components (an inner drive component and an outer drive component). Alternative coupler embodiments could have three or more drive components. In further alternatives, a coupler embodiment could have one drive component.

The various coupler embodiments disclosed herein can be utilized to simplify various surgical procedures. For example, in those implementations in which medical device is a robotic surgical device, a quick-change coupler on an arm of the surgical device could allow for exchanging end effectors while the arm of the device is positioned within a cavity of the patient. In one such situation, a separate device having at least one additional end effector positioned thereon is positioned in the patient's cavity and operates in conjunction with the device arm and coupler to effect the exchange of one end effector for another on the arm. Alternatively, a separate external device can be inserted into the patient's cavity through a separate or auxiliary port and/or trocar and operates to remove or un-install the end effector from the arm of the robotic device and retract it from the cavity. The new end effector is then attached to the external tool, the tool is re-inserted into the cavity, and the tool operates in conjunction with the device arm to install or attach the new end effector to the coupler.

Although the various implementations herein been described with reference to preferred embodiments, persons skilled in the art will recognize that changes may be made in form and detail without departing from the spirit and scope of the inventions.

What is claimed is:

1. A coupling apparatus for a medical device, the apparatus comprising:
    (a) a coupler body;
    (b) a cavity defined in a distal end of the coupler body;
    (c) a rotatable drive component disposed within the cavity, the drive component comprising:
        (i) an inner drive component comprising at least two inner pin-receiving openings; and
        (ii) an outer drive component comprising at least two outer pin-receiving openings; and
    (d) an actuable locking ring disposed around the cavity.

2. The coupling apparatus of claim 1, wherein the coupler body is coupleable to a tool, wherein the tool comprises:
    (a) a tool body sized and arranged to be positionable within the cavity;
    (b) a rotatable driven component operably coupled to the tool body, the rotatable driven component comprising:
        (i) at least two pin chambers defined in the rotatable driven component; and
        (ii) at least two tensioned pins, wherein each of the at least two tensioned pins is disposed within and is extendable from one of the at least two pin chambers comprising at least two tensioned pins extending therefrom,
    wherein the rotatable driven component is alignable with the rotatable drive component such that the at least two tensioned pins extend into the at least two pin-receiving openings.

3. The coupling apparatus of claim 1, wherein the coupler body is coupleable to a tool, wherein the tool comprises:
    (a) a tool body sized and arranged to be positionable within the cavity; and
    (b) a rotatable driven component operably coupled to the tool body, the rotatable driven component comprising:
        (i) an inner driven component comprising at least two inner pin chambers defined in the inner driven component and at least two inner tensioned pins disposed within and extendable from the at least two inner pin chambers; and
        (ii) an outer driven component comprising at least two outer pin chambers defined in the outer driven component and at least two outer tensioned pins disposed within and extendable from the at least two outer pin chambers;
    wherein the inner driven component is alignable with the inner drive component such that the at least two inner tensioned pins extend into the at least two inner pin-receiving openings, and
    wherein the outer driven component is alignable with the outer drive component such that the at least two outer tensioned pins extend into the at least two outer pin-receiving openings.

4. The coupling apparatus of claim 1, further comprising an insulation layer disposed between the inner and outer drive components.

5. A coupling apparatus for a medical device, the apparatus comprising:
    (a) a coupler body;
    (b) a cavity defined in a distal end of the coupler body;
    (c) a rotatable drive component disposed within the cavity, the drive component comprising at least two pin-receiving openings; and
    (d) an actuable locking ring disposed around the cavity, wherein the actuable locking ring is movable between a depressed position in which any tool body disposed within the cavity is releasable and a non-depressed position in which any tool body disposed within the cavity is locked therein.

6. The coupling apparatus of claim 5, wherein the coupler body is coupleable to a tool, wherein the tool comprises:
    (a) a tool body sized and arranged to be positionable within the cavity;
    (b) a rotatable driven component operably coupled to the tool body, the rotatable driven component comprising:
        (i) at least two pin chambers defined in the rotatable driven component; and
        (ii) at least two tensioned pins, wherein each of the at least two tensioned pins is disposed within and is extendable from one of the at least two pin chambers comprising at least two tensioned pins extending therefrom,
    wherein the rotatable driven component is alignable with the rotatable drive component such that the at least two tensioned pins extend into the at least two pin-receiving openings.

7. The coupling apparatus of claim 5, wherein the rotatable drive component comprises:
    (a) an inner drive component comprising at least two inner pin-receiving openings; and
    (b) an outer drive component comprising at least two outer pin-receiving openings.

8. The coupling apparatus of claim 7, wherein the coupler body is coupleable to a tool, wherein the tool comprises:
    (a) a tool body sized and arranged to be positionable within the cavity; and (b) a rotatable driven component operably coupled to the tool body, the rotatable driven component comprising:
  (i) an inner driven component comprising at least two inner pin chambers defined in the inner driven component and at least two inner tensioned pins disposed within and extendable from the at least two inner pin chambers; and
  (ii) an outer driven component comprising at least two outer pin chambers defined in the outer driven component and at least two outer tensioned pins disposed within and extendable from the at least two outer pin chambers;
wherein the inner driven component is alignable with the inner drive component such that the at least two inner tensioned pins extend into the at least two inner pin-receiving openings, and
wherein the outer driven component is alignable with the outer drive component such that the at least two outer tensioned pins extend into the at least two outer pin-receiving openings.

9. The coupling apparatus of claim 7, further comprising an insulation layer disposed between the inner and outer drive components.

10. The coupling apparatus of claim 1, further comprising an elongate tube disposed through a length of the coupler body such that the rotatable drive component is disposed around a distal portion of the elongate tube, the elongate tube comprising a lumen in fluid communication with a distal opening of the elongate tube.

11. A coupling system for a medical device, the system comprising:
  (a) a coupling apparatus associated with the medical device, the apparatus comprising:
    (i) a coupler body;
    (ii) a cavity defined in a distal end of the coupler body;
    (iii) a rotatable drive component disposed within the cavity, the drive component comprising at least two pin-receiving openings; and
    (iv) an actuable locking ring disposed around the cavity; and
  (b) a tool body coupleable with the coupling apparatus, wherein the tool body is sized and arranged to be positionable within the cavity, the tool body comprising:
    (i) a rotatable driven component operably coupled to the tool body, the rotatable driven component comprising:
      (A) at least two pin chambers defined in the rotatable driven component; and
      (B) at least two tensioned pins disposed within and extendable from the at least two pin chambers,
  wherein the rotatable driven component is alignable with the rotatable drive component such that the at least two tensioned pins extend into the at least two pin-receiving openings.

12. The coupling system of claim 11, wherein the rotatable drive component comprises:
  (a) an inner drive component comprising at least two inner pin-receiving openings; and
  (b) an outer drive component comprising at least two outer pin-receiving openings.

13. The coupling system of claim 12, wherein the rotatable driven component comprises:
  (a) a rotatable inner driven component, wherein the at least two pin chambers comprise at least two inner pin chambers defined in the rotatable inner driven component, and wherein the at least two tensioned pins comprise at least two inner tensioned pins disposed within and extendable from the at least two inner pin chambers; and
  (b) a rotatable outer driven component, wherein the at least two pin chambers comprise at least two outer pin chambers defined in the rotatable outer driven component, and wherein the at least two tensioned pins comprise at least two outer tensioned pins disposed within and extendable from the at least two outer pin chambers
wherein the rotatable inner driven component is alignable with the inner drive component such that the at least two inner tensioned pins extend into the at least two inner pin-receiving openings, and
wherein the rotatable outer driven component is alignable with the outer drive component such that the at least two outer tensioned pins extend into the at least two outer pin-receiving openings.

14. The coupling system of claim 12, further comprising an insulation layer disposed between the inner and outer drive components.

15. The coupling system of claim 11, wherein the actuable locking ring is movable between a depressed position in which the tool body is releasable from the cavity and a non-depressed position in which the tool body disposed within the cavity is locked therein.

16. The coupling system of claim 11, further comprising an elongate tube disposed through a length of the coupler body such that the rotatable drive component is disposed around a distal portion of the elongate tube, the elongate tube comprising a lumen in fluid communication with a distal opening of the elongate tube.

17. A coupling system for a medical device, the system comprising:
  (a) a coupling apparatus associated with the medical device, the apparatus comprising:
    (i) a coupler body;
    (ii) a cavity defined in a distal end of the coupler body;
    (iii) an inner drive component comprising at least two inner pin-receiving openings;
    (iv) an outer drive component comprising at least two outer pin-receiving openings; and
    (v) an actuable locking ring disposed around the cavity; and
  (b) a tool body coupleable with the coupling apparatus, wherein the tool body is sized and arranged to be positionable within the cavity, the tool body comprising:
    (i) a rotatable inner driven component comprising:
      (A) at least two inner pin chambers defined in the rotatable inner driven component, and
      (B) at least two inner tensioned pins disposed within and extendable from the at least two inner pin chambers; and
    (ii) a rotatable outer driven component comprising:
      (A) at least two outer pin chambers defined in the rotatable outer driven component; and
      (B) at least two outer tensioned pins disposed within and extendable from the at least two outer pin chambers,
  wherein the rotatable inner driven component is alignable with the inner drive component such that the at least two inner tensioned pins extend into the at least two inner pin-receiving openings, and
  wherein the rotatable outer driven component is alignable with the outer drive component such that the at least two outer tensioned pins extend into the at least two outer pin-receiving openings.

18. The coupling system of claim 17, further comprising an insulation layer disposed between the inner and outer drive components.

19. The coupling system of claim 17, wherein the actuable locking ring is movable between a depressed position in which the tool body is releasable from the cavity and a non-depressed position in which the tool body disposed within the cavity is locked therein.

20. The coupling system of claim 17, further comprising an elongate tube disposed through a length of the coupler body such that the rotatable drive component is disposed around a distal portion of the elongate tube, the elongate tube comprising a lumen in fluid communication with a distal opening of the elongate tube.

* * * * *